(12) United States Patent
Krug et al.

(10) Patent No.: US 8,158,083 B2
(45) Date of Patent: *Apr. 17, 2012

(54) PRECISION LIQUID DISPENSING SYSTEM

(75) Inventors: Robert E. Krug, Naperville, IL (US);
William Austhof, Oswego, IL (US);
Dennis Makowski, Yorkville, IL (US);
Daniel L. Bantz, Naperville, IL (US);
Marek Turewica, Lake Forest, IL (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 25 days.

This patent is subject to a terminal disclaimer.

(21) Appl. No.: 12/169,148

(22) Filed: Jul. 8, 2008

(65) Prior Publication Data

US 2009/0010810 A1 Jan. 8, 2009

Related U.S. Application Data

(63) Continuation of application No. 10/347,085, filed on Jan. 17, 2003, now Pat. No. 7,410,615.

(60) Provisional application No. 60/351,700, filed on Jan. 24, 2002.

(51) Int. Cl.
*B01L 3/02* (2006.01)
*G01N 1/10* (2006.01)

(52) U.S. Cl. ........ 422/509; 422/500; 422/501; 422/504; 422/521; 422/537; 422/539; 436/180

(58) Field of Classification Search .................. 422/100, 422/103, 500–501, 509, 537, 539, 504, 521; 436/180
See application file for complete search history.

(56) References Cited

U.S. PATENT DOCUMENTS

| 967,938 | A | 8/1910 | Krause |
|---|---|---|---|
| 3,650,306 | A | 3/1972 | Lancaster |
| 4,176,792 | A | 12/1979 | McCardle, Jr. |
| 4,311,667 | A | 1/1982 | Gocho |
| 4,351,799 | A | 9/1982 | Gross et al. |
| 4,459,267 | A | 7/1984 | Bunce et al. |
| 4,764,044 | A | 8/1988 | Konose |
| 4,818,706 | A | 4/1989 | Starr |
| 5,052,174 | A | 10/1991 | Bak |
| 5,055,263 | A | 10/1991 | Meltzer |
| 5,163,010 | A | 11/1992 | Klein et al. |

(Continued)

FOREIGN PATENT DOCUMENTS

EP 1093842 10/1999

(Continued)

OTHER PUBLICATIONS website at www.cpcpkg.com.

(Continued)

*Primary Examiner* — Brian R Gordon
(74) *Attorney, Agent, or Firm* — Lando & Anastasi, LLP

(57) ABSTRACT

A system for dispensing microdrops of reagent in small, precisely metered quantities maintains the fluid reagent to be dispensed in a reservoir under a controlled pressure. The reagent is dispensed through multiple nozzles connected to solenoid-actuated valves that control the flow of the reagent from the reservoir to the nozzles. Each valve is connected to one of the nozzles and electrical pulses are supplied separately to each of the valves to separately control the opening and closing of each valve to dispense predetermined quantities of the reagent through each nozzle at predetermined times.

18 Claims, 2 Drawing Sheets

U.S. PATENT DOCUMENTS

| | | | |
|---|---|---|---|
| 5,356,041 | A | 10/1994 | Hellenberg et al. |
| 5,716,150 | A | 2/1998 | Gueret |
| 5,743,960 | A | 4/1998 | Tisone |
| 5,834,314 | A | 11/1998 | Gates et al. |
| 5,938,080 | A | 8/1999 | Haaser et al. |
| 6,016,791 | A | 1/2000 | Thomas et al. |
| 6,058,537 | A | 5/2000 | Larson |
| 6,063,339 | A | 5/2000 | Tisone et al. |
| 6,186,686 | B1 | 2/2001 | Neuner |
| 6,203,759 | B1 * | 3/2001 | Pelc et al. .................... 422/100 |
| 6,270,273 | B1 | 8/2001 | Ohba |
| 6,371,129 | B1 | 4/2002 | Le Bras-Brown et al. |
| 6,926,866 | B2 | 8/2005 | Sickinger et al. |
| 7,169,616 | B2 | 1/2007 | Johnson et al. |
| 7,410,615 | B2 | 8/2008 | Krug et al. |
| 2001/0016177 | A1 | 8/2001 | Pelc et al. |
| 2001/0047309 | A1 | 11/2001 | Bartholomew et al. |
| 2001/0053337 | A1 | 12/2001 | Doktycz et al. |
| 2002/0010528 | A1 | 1/2002 | Bartholomew et al. |
| 2002/0064482 | A1 | 5/2002 | Tisone et al. |
| 2002/0072122 | A1 | 6/2002 | Copeland et al. |
| 2002/0159919 | A1 | 10/2002 | Churchill et al. |
| 2002/0176801 | A1 | 11/2002 | Giebeler et al. |
| 2003/0113233 | A1 | 6/2003 | Nanthakumar |
| 2003/0215957 | A1 | 11/2003 | Lemmo et al. |
| 2004/0241050 | A1 | 12/2004 | Bogen et al. |

FOREIGN PATENT DOCUMENTS

| | | |
|---|---|---|
| EP | 1093842 A1 | 4/2001 |

OTHER PUBLICATIONS

European Search Report for International Application No. EP 03 00 1337 dated Mar. 26, 2003.

* cited by examiner

PRECISION LIQUID DISPENSING SYSTEM

PRIORITY CLAIM

The present application is a continuation of U.S. application Ser. No. 10/347,085 filed Jan. 17, 2003, and issued as U.S. Pat No. 7,410,615 which claims priority from U.S. Provisional Application No. 60/351,700 filed Jan. 24, 2002, and entitled "PRECISION LIQUID DISPENSING SYSTEM."

BACKGROUND OF THE INVENTION

The invention relates generally to systems for depositing small amounts of liquid having volumes in the range of about 0.5 µL to 2 mL. Although there are various end uses for such systems, they are particularly useful in connection with microscale chemical and biological analyses. Frequently, the microdispensing system will be used to dispense reagent into a microplate having an array of small wells which hold liquid. A common size is a 96 well plate, measuring about 80 by 120 mm and having round sample wells having a diameter of about 6.5 mm. More recently, plates having 384 and 1536 wells have become available, and the wells in such plates are correspondingly smaller. Thus, reagents must be dispensed in extremely small quantities, and achieving dispensing accuracy and repeatability becomes increasingly difficult.

Depositing small droplets of liquid for various purposes, including ink jet printing has been of interest in recent years. For example, in U.S. Pat. No. 5,743,960 a system using a solenoid valve is employed. The system features the use of a positive displacement pump to provide the needed flow while the solenoid valve is opened and closed to form the desired droplet size, said to be in the range of 1-4 nanoliters (1-4 mL). Substitution of a piezoelectric dispenser for the solenoid valve dispenser was suggested. The volume of liquid deposited was intended to be in the range of $0.42 \times 10^{-9}$ to $2 \times 10^{-6}$ liters (0.42 mL to 2 µL).

Another patent disclosing the use of a positive displacement pump to supply a piezoelectric dispensing nozzle is U.S. Pat. No. 6,203,759. In an alternative system, a reservoir containing a liquid is maintained at a desired pressure. In both types of dispensing systems a sample typically is aspirated into the piezoelectric nozzle and then dispensed, using a liquid different from that being dispensed.

SUMMARY OF THE INVENTION

In accordance with the present invention, a system is provided for dispensing microdrops of reagent in small, precisely metered quantities from a reagent reservoir containing a fluid reagent to be dispensed. The reagent in the reservoir is maintained under a controlled pressure, and is supplied to multiple nozzles for dispensing microdrops of the reagent. Multiple solenoid-actuated valves are connected between the reservoir and the nozzles for controlling the flow of the reagent from the reservoir to the nozzles, with each valve being connected to one of the nozzles. Electrical pulses are supplied separately to each of the solenoid valves to separately control the opening and closing of each valve to dispense predetermined quantities of the reagent through each nozzle at predetermined times.

In a preferred embodiment of the invention, the reagent in the reservoir is maintained under a controlled pressure by an air pump that supplies pressurized air to the reservoir. An electrical control signal is supplied to the pump to control the pressure of the air supplied by the pump to the reservoir. A transducer senses the pressure within the reservoir and produces a signal representing that pressure. A closed-loop control system uses the transducer signal in a PID algorithm to maintain the desired pressure in the reservoir by regulating the electrical control signal supplied to the pump.

A preferred arrangement for controlling the solenoid valves permits selection of the desired volume of reagent to be dispensed from each nozzle, and a calibration table that specifies the widths of the electrical pulses required to dispense specified volumes of the reagent. When a desired volume not specified in the table is selected, a required pulse width is calculated from the pulse widths specified in the table for the two specified volumes closest to the selected desired volume. The calculation is preferably performed using linear interpolation between the two closest values in the table.

The invention provides improved accuracy and repeatability of dispensing, with the option of dispensing smaller volumes not currently available in commercial products utilizing solenoid valves. The invention allows dispensing in low volumes, e.g., from 0.5 µL to 2 mL, with full chemical compatibility with common chemical reagents used in biotechnology and chemical laboratories.

BRIEF DESCRIPTION OF THE DRAWINGS

The invention may best be understood by reference to the following description taken in conjunction with the accompanying drawings, in which.

DETAILED DESCRIPTION OF PREFERRED EMBODIMENTS

Although the invention will be described in connection with certain preferred embodiments, it will be understood that the invention is not limited to those particular embodiments. On the contrary, the invention is intended to include all alternatives, modifications and equivalent arrangements as may be included within the spirit and scope of the invention as defined by the appended claims.

Figure 1:
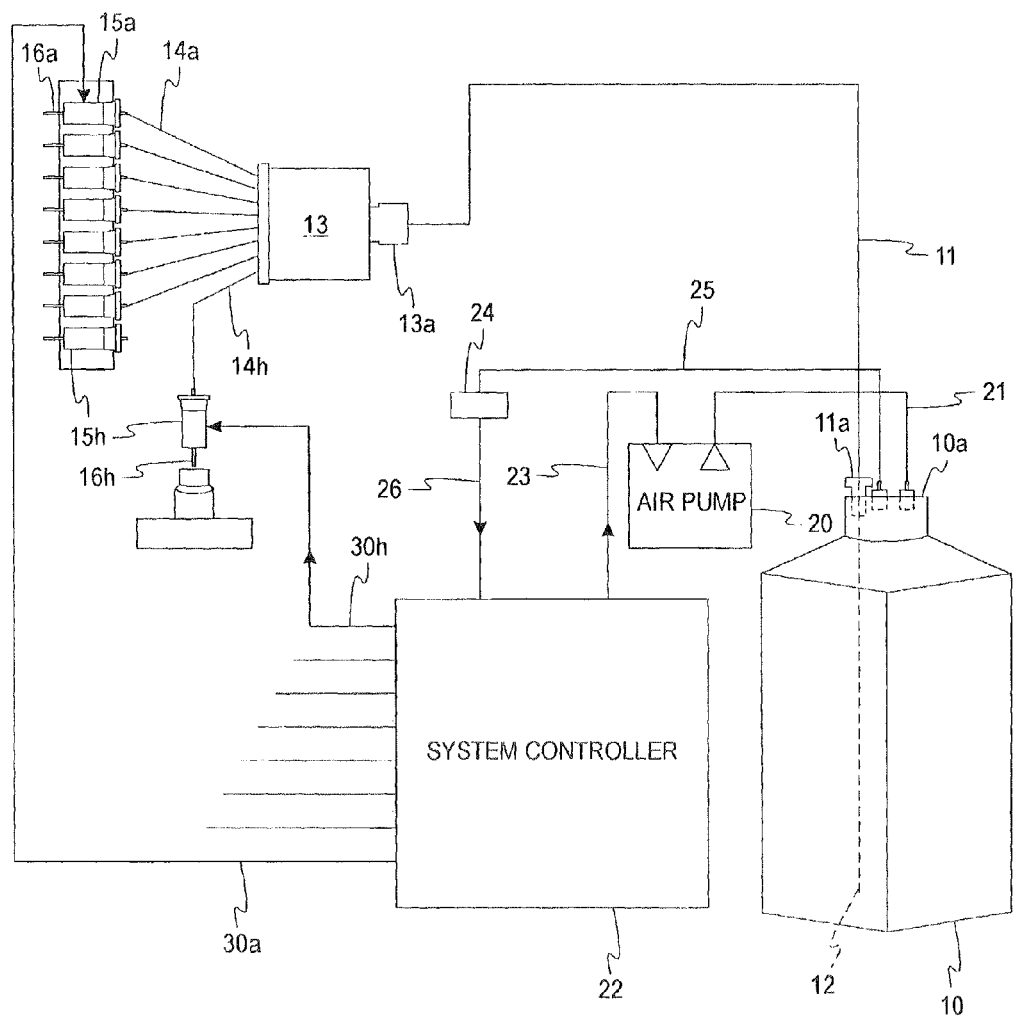
FIG. 1 is a block diagram of an eight-nozzle precision reagent-dispensing system embodying the invention.

Turning now to the drawings, and referring first to FIG. 1, the reagent to be dispensed is contained in a reservoir 10 (preferably a glass container) having a pressurized headspace at the top of the reservoir. An output line 11 leads from a supply line 12 near the bottom of the reservoir 10 to a manifold 13 having eight output lines 14*a*-14*h* leading to eight high-speed, solenoid-actuated valves 15*a*-15*h*. Each valve 15 carries a dispensing nozzle 16. Whenever one or more of the valves 15 is open, the pressure in the reservoir 10 forces reagent from the reservoir through the line 11 and the manifold 13. Manifold 13 is designed to allow equal flow distribution from the single output line 11 to the eight output line 14*a*-*h* and to the open valve(s) 15 is to the corresponding dispensing nozzle(s) 16. In a preferred embodiment, the manifold 13 is equipped with a bottom seal fitting 13*a*, has a fully swept internal liquid path to reduce the possibility of trapping air and is made of a polyaryletherketone ("PEEK") resin which provides good mechanical properties in combination with good resistance to the types of reagents commonly used in this type of equipment. The line 11 leading to the manifold 13 is preferably 0.125" ID, 0.1875" OD PFA Teflon® tubing, and the lines 14*a*-14*h* connecting the manifold 13 to the valves 15*a*-15*h* are preferably 0.040" ID, 0.0625" OD Tefzel® tubing. Lines 14*a*-14*h* and line 11 are coupled to the internals of manifold 13 in a manner that avoids unequal flow distribution, additional restrictions in metering, or trapping of air, all of which cause degradation of target dispense accuracy and precision.

The pressure within the reservoir 10 is controlled by an air pump 20 that supplies pressurized air to the reservoir via line 21 at a controlled pressure, e.g., about 5 psig (34.5 kPa gauge). The pump 20 preferably includes a brushless DC motor (with a three-wire control option) that is controlled by a system controller 22 via electrical line 23. The system controller 22 includes a microprocessor that receives a feedback signal from a transducer 24 sensing the pressure within the reservoir 10. The transducer 24 is connected to a pressure tap line 25 that comes off of the reservoir 10, and generates an electrical signal on line 26 corresponding to the pressure sensed by the transducer in the tap line 25. The pressure supply line 21, the pressure sensor tap line 25, and the reagent supply line 11 enter/exit the reagent reservoir 10 through a cap 10a. The lines 21 and 25 are attached to the cap 10a via barb fittings, while the liquid supply line 11 passes through the cap and is captured by a flangeless fitting 11a. The lines 21 and 25 are preferably 0.125" ID, 0.25" OD Tygon® tubing.

The microprocessor in the system controller 22 uses the signal from the transducer 24 in a standard PID (proportional, integral, derivative) control algorithm, to produce an output signal on line 23 to control the pressure within the reagent reservoir, preferably to within 0.02 psi. That is, the microprocessor continually compares the actual reservoir pressure, represented by the transducer signal on line 26, with the desired or "set point" pressure, e.g., 5 psig (34.5 kPa gauge), using the PID algorithm to produce the requisite output signal for maintaining the desired pressure in the reservoir 10. The pressure is maintained within a variation of about ±0.5%. A preferred minimum flow rate for the pump 20 is 500 ml/min. at a pressure of 5 psig.

The system controller 22 also produces the electrical pulses that control the times at which each of the valves 15a-15h is opened and closed. These pulses are generated on any of eight different output lines 30a-30h, each of which is connected to one of the solenoid-actuated valves 15a-15h. Each pulse rises from a differential voltage of zero to 24 DC volts spike pulse for 2 milliseconds, then reduces to a differential of 5 volts to hold open the valve 15 receiving that pulse, remains at the 5-volt level for a time period sufficient to dispense the selected volume of reagent through the opened valve, and then drops to a differential voltage of zero volts at the end of that time period to close the valve.

The desired volume of reagent to be dispensed from each nozzle 16 is selected by the user via a keypad or other manual input device on the front of a control panel (not shown). This manual input provides the microprocessor with a signal representing the selected volume. A memory associated with the microprocessor stores a calibration table that specifies the widths of the electrical pulses required to dispense specified volumes of the reagent. When a volume not specified in the table is selected, the microprocessor calculates a required pulse width from the pulse widths specified in the table for the two specified volumes closest to the selected volume. This calculation is preferably performed using linear interpolation between the two closest values in the table.

The calibration table is generated initially by supplying one of the solenoid-actuated valves with a succession of pulses of progressively increasing width, and measuring the actual volume of reagent dispensed through the nozzle connected to that valve. These measured volumes are stored in the table, along with the pulse width that produced each volume. Then when the user selects a desired volume, the microprocessor finds either that volume, or the two closest volumes in the table. If the exact value of the selected volume is in the table, the microprocessor generates a pulse having the width specified for that volume in the table. If the exact value is not in the table, then the microprocessor uses the two closest volume values, and their corresponding pulse widths, to calculate the pulse width required to dispense the volume selected by the user. Linear interpolation may be used for the calculation.

The solenoid-actuated valves used in the dispensing system may be selected on the basis of the specified minimum volume to be dispensed by the system. For example, if the specified minimum volume to be dispensed is 0.5 µL, a valve capable of dispensing a volume of approximately 0.125 µL is preferably selected, to allow for a four to one safety factor.

Figure 2:
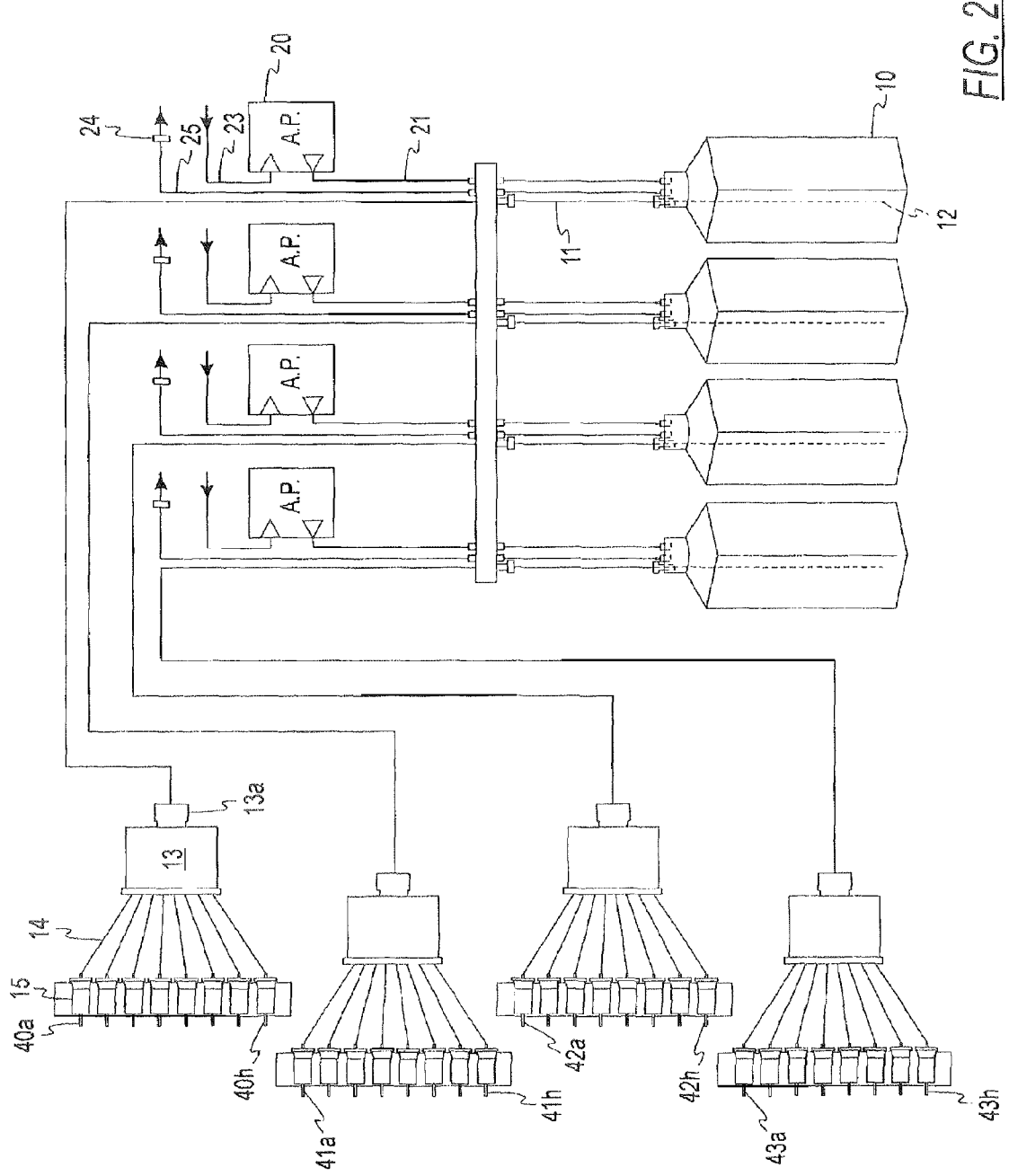
FIG. 2 is a block diagram of a 32-nozzle precision reagent-dispensing system embodying the invention.

FIG. 2 illustrates four dispensing systems of the type illustrated in FIG. 1 arranged in parallel to provide simultaneous dispensing of reagent from 32 nozzles 40a-40h, 41a-41h, 42a-42h and 43a-43h. This arrangement allows rapid filling of multiple wells in microplates having large numbers of wells.

In a test of the invention, a sample plate having 96 wells was used, each row of eight wells received sample liquid simultaneously. After each row received samples, the next row of wells received samples of the liquid and so on until all 96 wells had been sampled. Each of the eight valves (Lee Valve Company) opened for 5.0 milliseconds and dispensed 0.5 µL of the sample liquid into a well which had been primed with 199.5 µL of deionized water. After each plate had received 96 samples, the liquid delivery system was flushed and re-primed to simulate commercial practice and thus, to introduce potential variation in the amounts of liquid delivered to each well associated with changing or replenishing the dispensed liquid.

The liquid dispensed was a 5 g/L solution of a tartrazine yellow dye in deionized water, contained in a 1000 mL bottle, which was pressured to 5 psig ±0.02 (34.5 kPa). The arrangement of the tubing supplying liquid to each valve was made as uniform as possible. Measurement of the amount of liquid dispensed was done indirectly by reading the optical density of the liquid with a Spectracount® photometer (Packard Instrument Company). Values for the ten sample plates are shown in the following table.

| Plate No. | Mean Optical Density Reading | Coeff. Of Variation, % |
|---|---|---|
| 1 | 0.3738 | 1.23 |
| 2 | 0.3729 | 1.42 |
| 3 | 0.3725 | 1.32 |
| 4 | 0.3674 | 1.62 |
| 5 | 0.3723 | 1.44 |
| 6 | 0.3711 | 1.32 |
| 7 | 0.3676 | 1.61 |
| 8 | 0.3644 | 1.69 |
| 9 | 0.3698 | 1.50 |
| 10 | 0.3680 | 1.48 |

The mean value of the optical density measurements was 0.370 over all the 10 sample plates, with a standard deviation of 0.003 or coefficient of variation of 0.823%. Within individual sample plates, the minimum coefficient of variation was 1.231% on plate 1, while the maximum coefficient of variation was 1.686% on plate 8. The total variation from the mean optical density reading was about 1.25% across all the 10 sample plates. It should be evident that the system of the invention is capable of depositing the very precise and repeatable samples of liquids required for the tests typically carried out in such sample plates.

In one application of the dispensing system, the nozzles are mounted on a moveable support and moved in the Y plane into a location where the nozzle tips are aligned with the well of a microplate into which microdrops of the reagent are dispensed. The microplate is moved by a separate plate holder and displaced horizontally in the X plane. Thus, the nozzles are moved within the Y axis while the microplate that receives the microdrops moves in the X-axis directly and precisely under the nozzles. Alternatively, the nozzles may be stationary and the microplate moved under the nozzles. It is of course possible to move both the nozzles and the microplate for maximum flexibility and speed of operation.

In practice, it is not desirable to carry out such movements manually, using visual observation by the operator. To assure accuracy in repetitive steps of dispensing reagent into multiple wells, computer control of the movements of the nozzles and/or the microplate generally will be provided. The operator of the apparatus will instruct the instrument via a graphical user interface or by a separately linked computer to carry out a series of movements intended to transfer reagent from the reservoir to the microplate. It will be appreciated that such a sequence of movements may take place in three dimensions, usually called X and Y defining the position in a horizontal plane and Z defining the position in the vertical direction.

While the present invention has been described with reference to one or more embodiments, those skilled in the art will recognize that many changes may be made there to without departing from the spirit and scope of the present invention. Each of these embodiments and obvious variations thereof are contemplated as falling within the spirit and scope of the claimed invention, which is set forth in the following claims.

The invention claimed is:

1. A system for dispensing of reagent, said system comprising:
   a first reservoir containing a fluid reagent to be dispensed,
   an air pressure regulating device coupled to said first reservoir for maintaining said fluid reagent under a controlled air pressure,
   multiple nozzles each in fluid communication with said first reagent reservoir for dispensing said fluid reagent,
   multiple solenoid valves connected between said reservoir and said nozzles for controlling the flow of said fluid reagent from said first reservoir to said nozzles, each of said valves being connected to one of said nozzles, and
   a system controller connected to said solenoid valves and configured to receive a separate dispense volume for each of the multiple nozzles and further configured to provide electrical pulses separately to each of said solenoid valves to separately control the opening and closing of each valve to dispense the separate dispense volume of reagent through each of said nozzles, wherein the controller is further configured to set a pulse width for the electrical pulses based on the separate dispense volume for each of the multiple nozzles;
   wherein the system is configured such that the controlled air pressure causes fluid reagent to be dispensed through a nozzle upon opening of a corresponding one of the multiple solenoid valves.

2. A system of claim 1 wherein said air pressure regulating device comprises an air pump connected to said first reservoir for supplying pressurized air to said first reservoir, said system controller is connected to said pump for controlling pressure of the air supplied by said pump to said first reservoir, and said air pressure regulating device comprises a transducer sensing pressure in said first reservoir and supplying said system controller with a signal representing the pressure in said first reservoir.

3. A system of claim 1 wherein said system controller includes a calibration table that specifies pulse widths of said electrical pulses required to dispense specified volumes of said fluid reagent, and wherein the system controller is further configured to determine that a desired dispense volume is not contained in the calibration table and calculate a required pulse width from pulse widths specified in said calibration table.

4. A system of claim 2 wherein the pressure in said first reservoir is maintained within a variation of about ±0.5% about a set point pressure.

5. A system of claim 4 wherein the pressure in said first reservoir is about 5 psig ±0.02 (34.5 kPa gauge).

6. A system of claim 3 wherein the system controller is configured to calculate said required pulse width based on linear interpolation using two dispense volumes contained in the calibration table.

7. The system of claim 3 wherein the calibration table includes at least one dispense volume in the range of about 0.5 µL to 2 mL.

8. A system of claim 3 wherein at least one of said electrical pulses provided to one of the solenoid valves comprises a spike pulse portion having a voltage level followed by an electrical pulse portion having a voltage level less than the voltage level of the spike pulse portion.

9. A system of claim 8 wherein said spike pulse portion has a voltage level of about 24 vDC for 2 milliseconds and the lower electrical pulse portion has a voltage level of about 5 vDC.

10. A method of dispensing a fluid reagent from a first reagent reservoir containing the fluid reagent to be dispensed using a controller, said method comprising
    using pressurized air pump coupled to the reservoir to maintain said reagent under a controlled pressure in said reservoir,
    supplying said reagent from said reservoir to multiple solenoid-actuated valves connected to the reservoir and to multiple nozzles for dispensing the reagent, said solenoid-actuated valves, under the control of the controller, controlling flow of the reagent from said reservoir to said nozzles, with each valve being connected to one of said nozzles and with each nozzle being in fluid communication with the first reagent reservoir,
    receiving a separate desired dispense volume for each of the multiple nozzles;
    determining an electrical pulse width corresponding to each separate desired dispense volume; and
    supplying electrical pulses having the determined electrical pulse widths separately to each of said solenoid valves to separately control the opening and closing of each valve to dispense predetermined quantities of said reagent through each nozzle at predetermined times.

11. The method of claim 10 wherein determining an electrical pulse width includes:
    providing a calibration table that specifies electrical pulse widths of electrical pulses required to dispense specified volumes of said reagent,
    determining that one of the separate desired dispense volumes is not contained in the calibration table, and
    calculating an electrical pulse width corresponding to the one of the separate desired dispense volumes based on two electrical pulse widths contained in the calibration table.

12. The method of claim 10 further comprising:
    supplying an electrical control signal to said air pump to control the pressure of the air supplied by said pump to said reservoir, sensing the pressure within the reservoir and producing a signal representing that pressure, and using a closed-loop control system that receives said transducer signal and uses a proportional, integral, derivative control algorithm to maintain a desired pressure in said reservoir by regulating said electrical control signal supplied to said pump.

13. A method of claim 12 wherein said desired pressure of said reservoir is maintained within a variation of about ±0.5% about a set point pressure.

14. The method of claim 12 wherein said desired pressure is about 5 psig ±0.4 (34.5 kPa gauge).

15. The method of claim 11 wherein said electrical pulse width corresponding to the one of the separate desired dispense volumes is calculated by linear interpolation of two electrical pulse widths contained in the calibration table.

16. A method of claim 10 wherein each of the desired separate dispense volumes is in the the range of about 0.5 µL to 2 mL.

17. A method of claim 11 wherein said electrical pulse corresponding to the one of the separate desired dispense volumes comprises a spike pulse having a voltage level, followed by a lower pulse for a period of time required to dispense the one of the separate desired dispense volumes; wherein the lower pulse has a voltage level less than the voltage level of the spike pulse.

18. A method of claim 17 wherein said spike pulse is about 24 vDC for 2 milliseconds followed by a lower electrical pulse of about 5 vDC.

* * * * *